United States Patent
Ball et al.

(10) Patent No.: US 9,808,630 B2
(45) Date of Patent: Nov. 7, 2017

(54) METHODS, DEVICES, AND SYSTEMS FOR COMMUNICATING WITH AN IMPLANTABLE MEDICAL DEVICE OF A LAST FAR FIELD COMMUNICATION SESSION DURING A SUBSEQUENT FAR FIELD COMMUNICATION SESSION WHILE USING A SAME SESSION KEY

(71) Applicant: MEDTRONIC, INC., Minneapolis, MN (US)

(72) Inventors: Warren W. Ball, Coon Rapids, MN (US); Ajinkya M. Joglekar, Maple Grove (IN); Nathan A. Torgerson, Andover, MN (US); Matthew L. Plante, Stacy, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 61 days.

(21) Appl. No.: 14/695,037

(22) Filed: Apr. 23, 2015

(65) Prior Publication Data

US 2015/0306404 A1  Oct. 29, 2015

Related U.S. Application Data

(60) Provisional application No. 61/983,886, filed on Apr. 24, 2014.

(51) Int. Cl.
*A61N 1/00* (2006.01)
*A61N 1/372* (2006.01)
(Continued)

(52) U.S. Cl.
CPC ..... *A61N 1/37217* (2013.01); *A61N 1/37252* (2013.01); *H04B 13/005* (2013.01); *H04L 67/12* (2013.01)

(58) Field of Classification Search
CPC ............ A61N 1/37217; A61N 1/37252; H04B 13/005; H04L 67/12
See application file for complete search history.

(56) References Cited

U.S. PATENT DOCUMENTS 5,887,063 A  3/1999  Varadharajan et al.
6,443,891 B1  9/2002  Grevious
(Continued)

OTHER PUBLICATIONS

Sagan, "RF Integrated Circuits for Medical Applications: Meeting of Ultra Low Power Communication", Zarlink Semiconductor, http://stf.ucsd/edu/presentations/2007/2007-08%20STF%20%20Zarlink%20ULP%20transceivers.pdf, Jun. 2007.

(Continued)

*Primary Examiner* — Lindsey G Wehrheim
(74) *Attorney, Agent, or Firm* — Withers & Keys, LLC

(57) ABSTRACT

An external device transfers a key to an implantable medical device over a proximity communication and then establishes a first far field communication session with the implantable medical device where the key is used for the first communication session. This first communication session may occur before implantation while the implantable medical device is positioned outside of the sterile field so that using a proximity communication is easily achieved. Once the implantable medical device is passed into the sterile field for implantation, the external device may then establish a second far field communication session with the implantable medical device where the last key that was used for the first communication session is again used for the second communication session which avoids the need for another proximity communication to occur within the sterile field.

17 Claims, 6 Drawing Sheets

(51) Int. Cl.
*H04B 13/00* (2006.01)
*H04L 29/08* (2006.01)

(56) References Cited

U.S. PATENT DOCUMENTS

| | | |
|---|---|---|
| 6,738,670 B1 | 5/2004 | Almendinger et al. |
| 7,039,810 B1 | 5/2006 | Nichols |
| 7,155,290 B2 | 12/2006 | Von Arx et al. |
| 7,187,978 B2 | 3/2007 | Malek et al. |
| 7,831,828 B2 | 11/2010 | Von Arx et al. |
| 8,265,770 B2 | 9/2012 | Toy et al. |
| 8,301,110 B2 | 10/2012 | Roberts et al. |
| 2005/0137652 A1 | 6/2005 | Cauller et al. |
| 2005/0203582 A1 | 9/2005 | Healy et al. |
| 2008/0154331 A1 | 6/2008 | John et al. |
| 2010/0179451 A1 | 7/2010 | Hately et al. |
| 2011/0172741 A1 | 7/2011 | Roberts et al. |
| 2011/0288615 A1 | 11/2011 | Armstrong et al. |
| 2012/0197347 A1 | 8/2012 | Olson et al. |
| 2012/0271380 A1* | 10/2012 | Roberts .............. A61N 1/37252 607/60 |

OTHER PUBLICATIONS

PCT/US15/027404 search report and written opinion dated Jul. 9, 2015.

* cited by examiner

METHODS, DEVICES, AND SYSTEMS FOR COMMUNICATING WITH AN IMPLANTABLE MEDICAL DEVICE OF A LAST FAR FIELD COMMUNICATION SESSION DURING A SUBSEQUENT FAR FIELD COMMUNICATION SESSION WHILE USING A SAME SESSION KEY

RELATED APPLICATIONS

The present application claims priority to U.S. Provisional Application No. 61/983,886, filed on Apr. 24, 2014, and having the title METHODS, DEVICES, AND SYSTEMS FOR COMMUNICATING WITH AN IMPLANTABLE MEDICAL DEVICE OF A LAST FAR FIELD COMMUNICATION SESSION DURING A SUBSEQUENT FAR FIELD COMMUNICATION SESSION WHILE USING A SAME SESSION KEY.

TECHNICAL FIELD

Embodiments relate to systems where an external device communicates with an implantable medical device via a far field communication session. More particularly, embodiments relate to systems where the external device communicates with an implantable medical device that is the last device to which the external device has previously communicated while using the same session key.

BACKGROUND

Implantable medical devices (IMDs) provide electrical stimulation and/or drug therapy to patients to address medical issues. The IMD is implanted within the body of the patient at a convenient location such as within the abdomen or within the upper torso. An implantable medical lead is coupled to the IMD and may be routed from the site of the implantable medical device to a target site where the electrical stimulation is provided to the tissue, such as within the spinal column, within the brain, and so forth. The IMD generates electrical stimulation signals that are carried by an electrical conductor within the lead to electrodes located at a distal region of the lead that are positioned at the target site.

In order to implant the IMD, a surgical procedure is used where a sterile field is provided about the body. Prior to passing the IMD into the sterile field, an external device may open a far field communication session with the IMD in order to perform preliminary tasks including transferring patient information to the IMD. For instance, the external device may open a MICS band communication session for this purpose. Often during this time, the patient is being prepped for the surgical procedure within the sterile field. Once the preliminary tasks are completed by the external device, the external device may then terminate the communication session. Closing the communication session preserves the battery life of the IMD by allowing the far field communication circuit to sleep. The IMD is then passed into the sterile field and is surgically implanted within the body of the patient.

Once the IMD has been implanted, the external device is then used to open another far field communication session with the IMD. The external device may communicate with the IMD to initiate integrity checks of the leads that are connected to the IMD. The external device may also communicate with the IMD to program the stimulation therapy parameters. The communication session may then be closed and the surgical procedure is concluded.

Because the external device utilizes far field communications with the IMD, it is desirable to ensure that the external device is communicating with the intended IMD. Other IMDs may also be in range of the far field signals of the external device, and the external device should avoid opening far field communication sessions with these other IMDs. To ensure that the external device is communicating with the correct IMD, the external device may use a proximity communication such as a near field inductive communication via a near field wand that only the intended IMD is able to receive. The proximity communication may transfer a unique key from the external device to the IMD. The external device may then ensure that the key is being used by the IMD that is responding via the far field communications such as for encryption purposes or to otherwise identify the communications from the IMD.

This transfer of the key via the proximity communication ensures that the external device is communicating with the correct IMD. However, because the external device of this scenario is not permanently bonded to the IMD, the external device attempts to exchange a new key each time a far field communication session is attempted. Therefore, when the external device attempts to start a far field communication session with the IMD while the IMD is located within the sterile field, the proximity communication requires that the proximity wand be introduced into the sterile field. This introduces additional burdens and delay into the implantation process.

SUMMARY

Embodiments address issues such as these and others by providing external devices that utilize a key provided to a last device for which a far field communication session was established when an attempt to exchange a new key via a proximity communication fails. Therefore, when the external device attempts to communicate with the IMD once the IMD is in the sterile field, the proximity wand may be kept outside the sterile field such that the proximity communication fails. The external device then attempts to start the communication session where the key used in the last communication session is again used in the present communication session. Because the IMD has retained the key used in the last communication session that occurred while the IMD was outside the sterile field, the IMD is able to enter the communication session with the external device while the IMD is in the sterile field without the IMD receiving a new key.

Embodiments provide a method of communicating with an implantable medical device. The method involves exchanging a key with the implantable medical device over a first proximity communication. The method further involves beginning a first far field communication session with the implantable medical device and exchanging communications during the first far field communication session with the implantable medical device where the implantable medical device implements the key when exchanging the communications. The method involves terminating the first far field communication session and attempting to exchange a second key over a second proximity communication after terminating the first communication session. Additionally, the method involves attempting to begin a second far field communication session where the external device expects communications of the second session, including a response to the attempt, to use the second key. If no response is received to the attempt to begin the second far field communication session which uses the second key, then the method further involves attempting to begin the second far field communication session where the external device expects communications of the second session, including the response to the attempt, to use the first key. If a response that uses the first key is received to the attempt to begin the second far field communication where the external device expects the response to use the first key, then the method further involves conducting the second far field communication session where communications of the second session use the first key.

Embodiments provide an external device that communicates with an implantable medical device. The external device includes a proximity communication circuit, a far field communication circuit, and a controller coupled to the proximity communication circuit and the far field communication circuit. The controller is configured to exchange a key with the implantable medical device over a first proximity communication. The controller is also configured to begin a first far field communication session with the implantable medical device and exchange communications during the first far field communication session with the implantable medical device where the implantable medical device implements the key when exchanging the communications. The controller is further configured to terminate the first far field communication session, attempt to exchange a second key over a second proximity communication after terminating the first communication session and attempt to begin a second far field communication session where the controller expects communications of the second session, including a response to the attempt, to use the second key. Additionally, the controller is configured such that if no response is received to the attempt to begin the second far field communication session that uses the second key, the controller then attempts to begin the second far field communication session where the controller expects communications of the second session, including the response to the attempt, to use the first key. If a response that uses the first key is received to the attempt to begin the second far field communication where the controller expects the response to use the first key, the controller then conducts the second far field communication session where communications of the second session use the first key.

Embodiments provide a system that includes an implantable medical device and an external device. The external device includes a proximity communication circuit, a far field communication circuit, and a controller coupled to the proximity communication circuit and the far field communication circuit. The controller is configured to exchange a key with the implantable medical device over a first proximity communication. The controller is also configured to begin a first far field communication session with the implantable medical device and exchange communications during the first far field communication session with the implantable medical device where the implantable medical device implements the key when exchanging the communications. The controller is further configured to terminate the first far field communication session, attempt to exchange a second key over a second proximity communication after terminating the first communication session and attempt to begin a second far field communication session where the external device expects communications of the second session, including a response to the attempt, to use the second key. Additionally, the controller is configured such that if no response is received to the attempt to begin the second far field communication session that uses the second key, the controller then attempts to begin the second far field communication session where the external device expects communications of the second session, including the response to the attempt, to use the first key. If a response that uses the first key is received to the attempt to begin the second far field communication where the external device expects the response to use the first key, the controller then conducts the second far field communication session where communications of the second session use the first key.

DETAILED DESCRIPTION

Embodiments allow an external device to exchange a key with an IMD while the IMD is outside of a sterile field by using a proximity communication and then use that key for a far field communication session with the IMD while the IMD remains outside of the sterile field and also for a second far field communication session with the IMD while the IMD resides within the sterile field. Thus, no proximity communication with the IMD is necessary while the IMD is within the sterile field in order to establish the far field communication session with the IMD.

Figure 1:
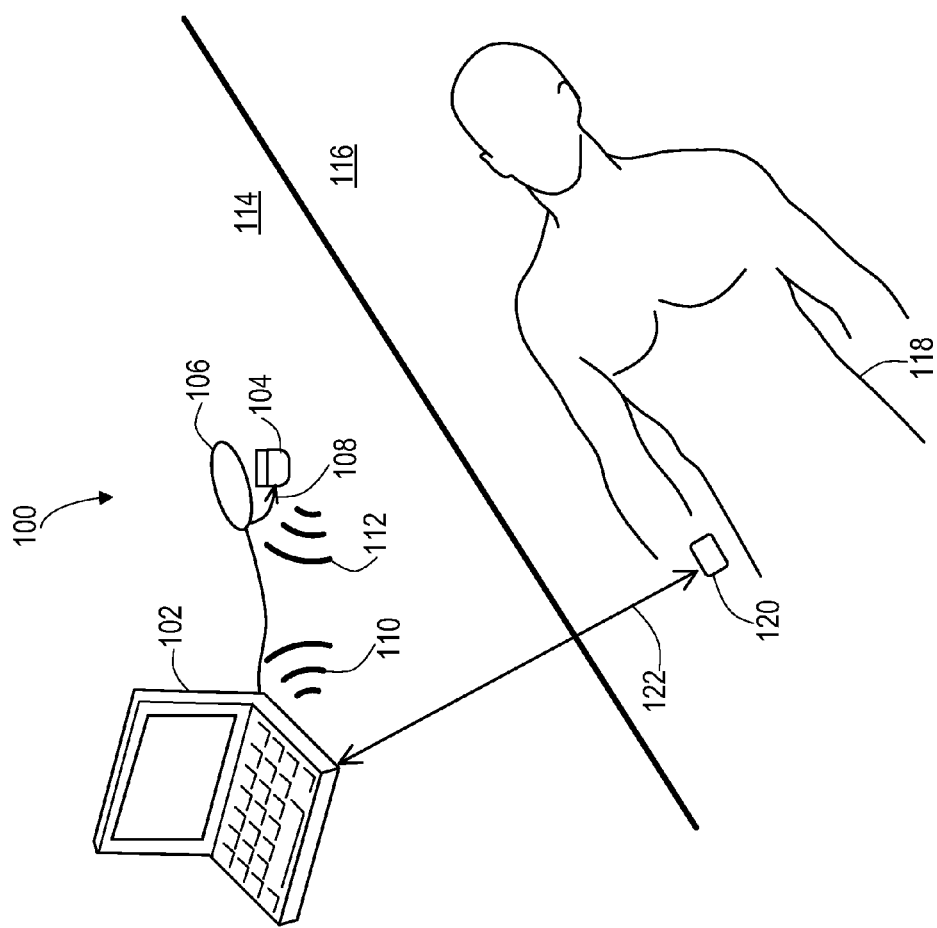
FIG. 1 shows an operating environment for embodiments of the medical system where the IMD is present outside of the sterile field.

FIG. 1 shows an example of an operating environment for the various embodiments. In this example, a system 100 includes an external device 102 and includes an IMD 104 that is being implanted into a patient 118. For the stage of the implantation procedure shown in FIG. 1, the external device 102 and the IMD 104 are in an area 114 outside of a sterile field area 116. While in the area 114 that is outside of the sterile field, initial preparation of the IMD 104 may be performed including transferring information about the patient 118 including an identification of the patient. The patient 118 is positioned within the sterile field area 116 and is being prepped for the implantation of the IMD 104 at this point. While the IMD 104 is located outside of the sterile field, the IMD 104 may be contained within a sterile packaging which does not interfere with the near field and far field communications. The IMD 104 is then removed from the sterile packaging when being introduced into the area 116 of the sterile field.

The external device 102 may initially communicate with an external stimulator 120 that may have previously been installed for the patient 118 for a trial period of stimulation therapy. The external device 102 may establish a communication link 122 with the external stimulator 120 which may be wired or wireless and may be near field or far field when wireless. The link 122 may be established while the external stimulator 120 remains attached to the patient 118 or may be established once the external stimulator 120 has been removed from the patient 118 and passed into the area 114 outside of the sterile field. The external device 102 may obtain patient information, therapy programming, and the like from the external stimulator 120.

The external device 102 also communicates with the IMD 104 while the IMD 104 is present in the area 114 outside of the sterile field. The external device 102 sends far field wireless signals 110, such as in the medical implant communication service (MICS) band, to the IMD 104 during a communication session. However, in order to establish the communication session, the external device 102 utilizes a proximity communication 108, such as a near field inductive coupling from a wand or hoop 106 positioned in close proximity to the IMD 104 to send a unique key to the IMD 104. Because the near field communication has a very limited range, only the intended IMD 104 is in range to receive the proximity communication containing the unique key. Therefore, when the external device 102 attempts to begin the far field communication session by sending the far field signals 110, the intended IMD 104 is the only IMD that can respond with far field communication signals 112 that utilize the unique key to identify the far field signals 112 as being from the intended IMD 104. For instance, the key may be used for encryption, as a header, or in any other manner that identifies the far field signals as being from an IMD possessing the unique key.

The external device 102 then proceeds to communicate with the intended IMD 104 via the far field signals 110, 112 to exchange information with the IMD 104. The information being exchanged may be basic setup information including the patient information. As mentioned above, this information for setup may have been obtained from the external stimulator 120 when present and/or may be entered by a user manually via a user interface at the external device 102. The external device 102 then closes the far field communication session with the IMD 104 such that the IMD 104 may turn off the far field communication circuits to conserve battery power.

Figure 2:
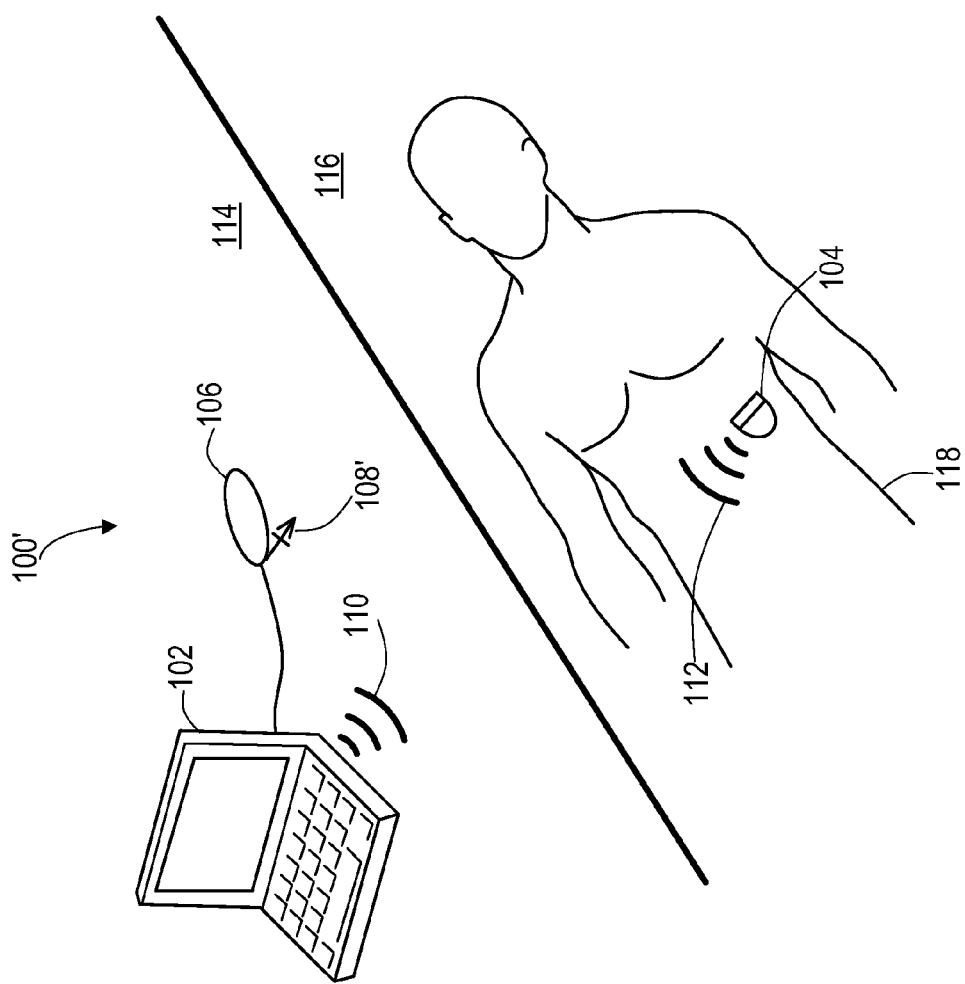
FIG. 2 shows the operating environment for embodiments of the medical system where the IMD is present inside of the sterile field.

The next stage of the implantation procedure involving the system 100' involves the IMD 104 which has been moved into the sterile field area 116 being implanted into the patient 118. This stage is shown in FIG. 2. Once the IMD 104 is implanted, a second far field communication session between the external device 102 and the IMD 104 is established. The external device 102 is for use by clinicians and is used to communicate with any IMD being implanted rather than being permanently bonded to a particular IMD. Therefore, the external device 102 looks to exchange a unique key for each far field communication session via a proximity communication 108'. However, at this stage of the implantation procedure, the proximity wand or hoop 106 remains in the area 114 outside of the sterile field and therefore the IMD 104 is no longer within range of the proximity communication 108'.

Rather than bringing the wand or hoop 106 into the sterile field area 116, the external device 102 retains the last used key so that it may be used in a subsequent communication with the same IMD 104 and attempts to use the last key when doing so is appropriate. Before attempting to use the last key for another session, the external device 102 first attempts the proximity communication 108' to exchange a new unique key and then attempts to start the second far field communication session of the implantation procedure via far field signals 110 based on the new key. The external device 102 requests a far field response from the IMD 104 where the external device 102 expects the new key to be used. However, the IMD 104 does not have the new key and cannot properly respond to the request for a response by the external device 102. The external device 102 reacts to the failure to receive a response from the IMD 104 that utilizes the new key by requesting a far field response from the IMD 104 where the external device 102 expects the last key used by the external device 102 to be used in the response.

Where the IMD 104 is the same IMD that communicated with the external device in the immediately prior far field communication session, which will be the case in the implantation procedure scenario being shown in FIGS. 1 and 2, the IMD 104 has the last key used by the external device 102. Therefore, the IMD 104 can properly respond to the request by the external device 102 to respond using the last used key. The second communication session then proceeds with the external device 102 sending far field signals 110 from the area 114 outside of the sterile field and the IMD 104 sending far field signals 112 from the area 116 within the sterile field.

Figure 3:
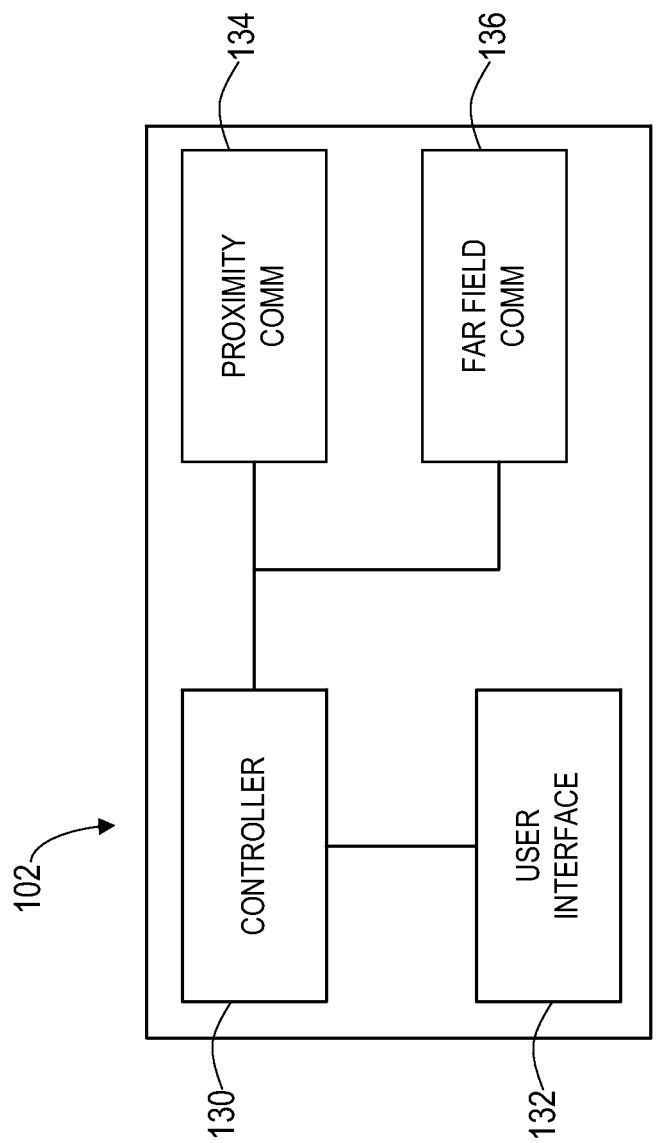
FIG. 3 shows an example of components for embodiments of an external device.

FIG. 3 shows an example of components for embodiments of the external device 102. The external device 102 includes a controller 130 that performs logical operations, such as those of FIGS. 5 and 6 which are discussed below, in order to establish the communication sessions with the IMD 104. The controller 130 may be of various forms such as a general purpose programmable processor, an application specific processor, hardwired digital logic, or combinations thereof.

The controller 130 communicates with other components of the external device 102. For instance, the controller 130 may be linked to a user interface 132, such as an input device that a user may manipulate to provide commands and information to the controller 130. The user interface 132 may include features such as a keyboard, a touch screen, a computer mouse, or combinations thereof.

The controller 130 also communicates with a proximity communication circuit 134 in order to provide the proximity communications 108 to send the unique key to the IMD 104. The proximity communication circuit 134 may include a coil tuned to an appropriate frequency for near field, inductive coupling and also include a driver to pass electrical signals through the coil. The proximity communication circuit 134 may be unidirectional for sending signals to the IMD 104. Alternatively, the proximity communication circuit 134 may be bi-directional for embodiments where the IMD 104 also has a bi-directional proximity communication circuit which allows the external device 102 to receive proximity communications sent by the IMD 104.

The controller 130 communicates with a far field communication circuit 136 in order to conduct the far field communication sessions with the IMD 104. The far field communication circuit 136 includes transmitting and receiving capabilities and is coupled to an antenna for outputting the wireless far field signals 110 and for receiving the wireless far field signals 112 sent by the IMD 104. These far field signals 110 may be at a significantly higher frequency than the signals of the near field proximity communications 108.

Figure 4:
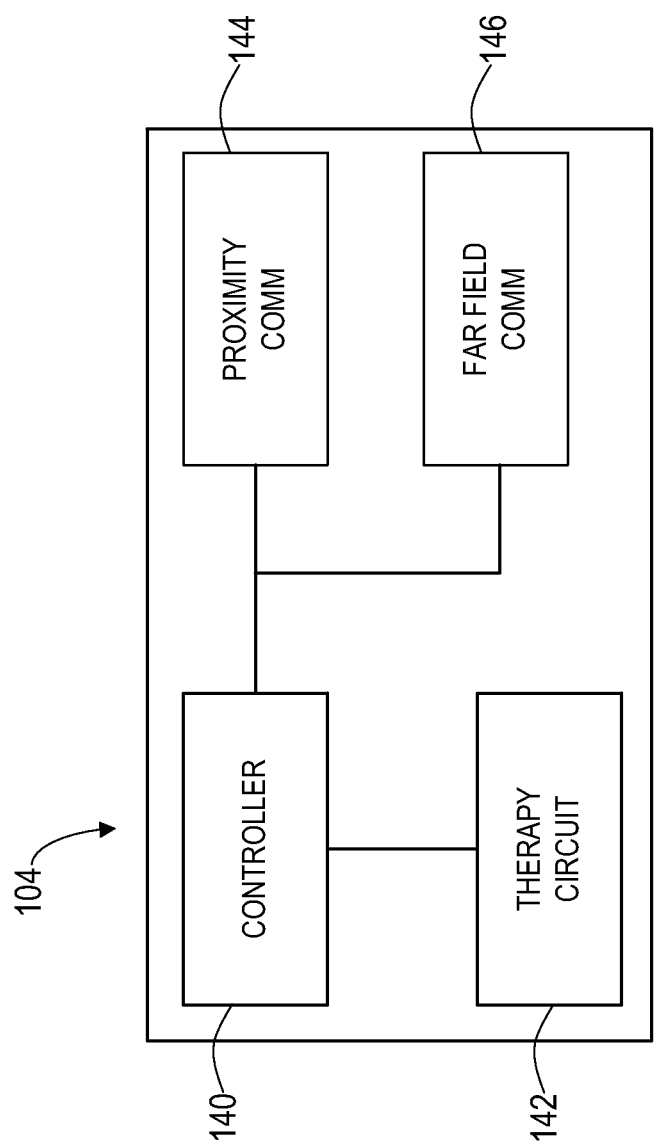
FIG. 4 shows an example of components for embodiments of an IMD.

FIG. 4 shows an example of components for embodiments of the IMD 104. The IMD 104 also includes a controller 140 that performs logical operations in order to establish the communication sessions with the external device 102. The controller 140 may also be of various forms such as a general purpose programmable processor, an application specific processor, hardwired digital logic, or combinations thereof.

The controller 140 communicates with other components of the IMD 104. For instance, the controller 140 may be linked to a therapy circuit 142 that includes a pulse generator for producing electrical stimulation pulses. The therapy circuit 142 is in turn connected to a medical lead to deliver the electrical stimulation pulses to the target site within the body 118. The controller 140 may control the pulse generator of the therapy circuit 142 in order to produce electrical stimulation signals that have characteristics specified by the therapy programming that has been provided from the external device 102 to the IMD 104. For instance, the controller 140 may control which electrodes receive a stimulation signal, the amplitude of the signal, the pulse width of the signal, and so forth.

The controller 140 also communicates with a proximity communication circuit 144 in order to receive the proximity communications 108 including the unique key sent by the external device 102. The proximity communication circuit 144 may include a coil tuned to an appropriate frequency for the near field, inductive coupling. The proximity communication circuit 144 may be unidirectional for receiving the signals from the external device 102. Alternatively, the proximity communication circuit 144 may be bi-directional for embodiments where the external device 102 also has a bi-directional proximity communication circuit which allows the IMD 104 to send proximity communications back to the external device 102.

The controller 140 communicates with a far field communication circuit 146 in order to conduct the far field communication sessions with the external device 102. The far field communication circuit 146 includes transmitting and receiving capabilities and is coupled to an antenna for outputting the wireless far field signals 112 and receiving the wireless far field signals 110 from the external device 102.

Figure 5:
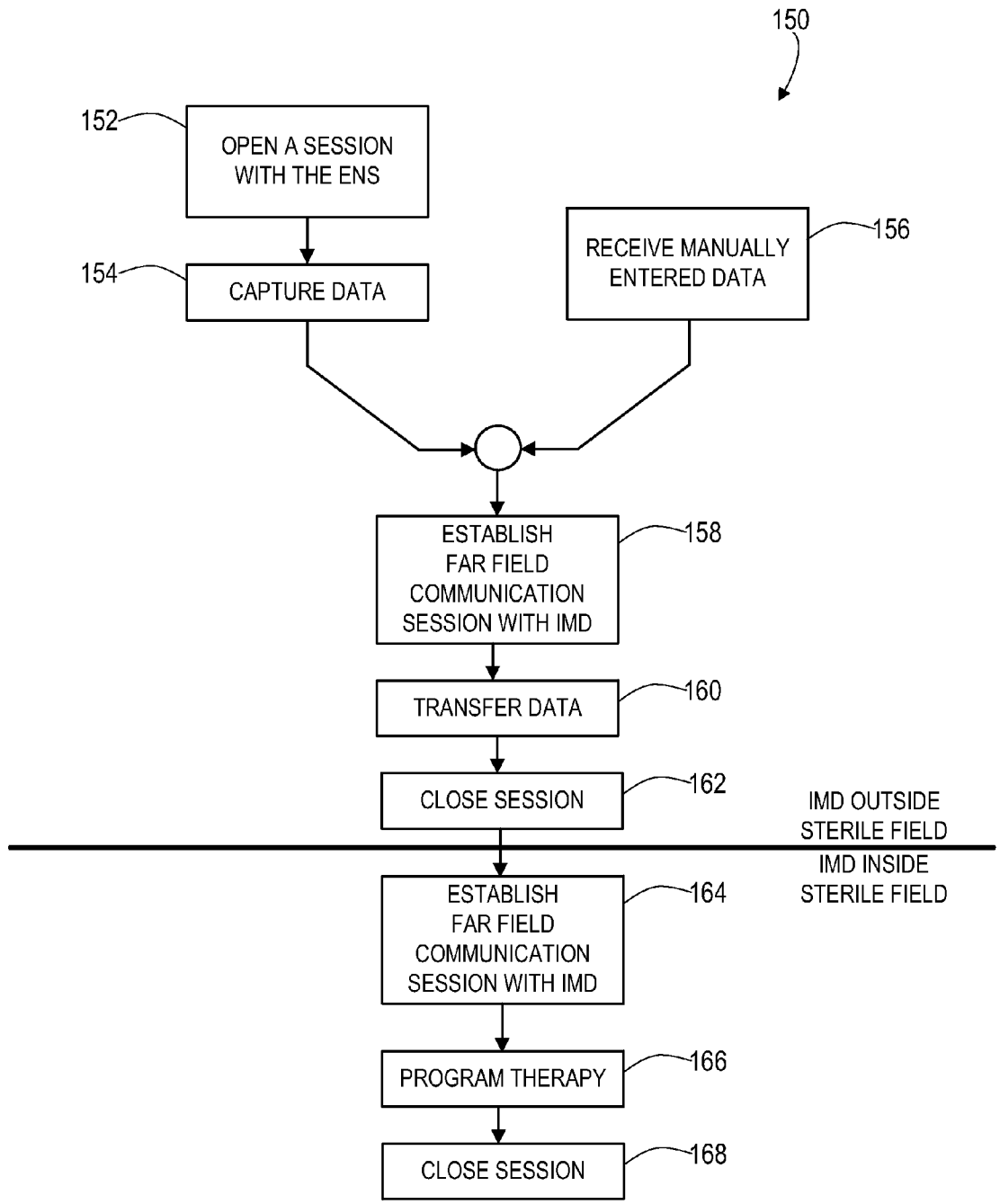
FIG. 5 shows an example of logical operations for embodiments of the external device to communicate with the IMD during the implantation procedure.

FIG. 5 shows an example of logical operations that may be performed by the external device 102 during the implantation procedure discussed above in relation to FIGS. 1 and 2. Initially, the external device 102 may open a communication session with an external stimulator (ENS) 120 at an operation 152 to obtain patient and therapy information when the external stimulator 120 is present. The external device captures the data from the external stimulator 120 at an operation 154. Additionally or alternatively, the external device may obtain patient information and other information for setup of the IMD 104 by receiving information that is manually entered by a clinician interacting with the user interface of the external device 102 at an operation 156.

While the IMD 104 is located outside of the sterile field, the external device 102 establishes a far field communication session with the IMD 104 at an operation 158. During the far field communication session, the external device 102 transfers setup data to the IMD 104 including patient information. The external device 102 then terminates the first far field communication session at operation 162.

The IMD 104 is then moved into the sterile field and is implanted into the patient 118. The external device 102 then establishes a second far field communication session with the IMD 104 at an operation 164. The external device 102 programs the therapy settings into the IMD 104 and instructs the IMD 104 to perform any integrity and performance testing at an operation 166. The IMD 104 then terminates the second far field session at an operation 168 to conclude the implantation procedure.

Figure 6:
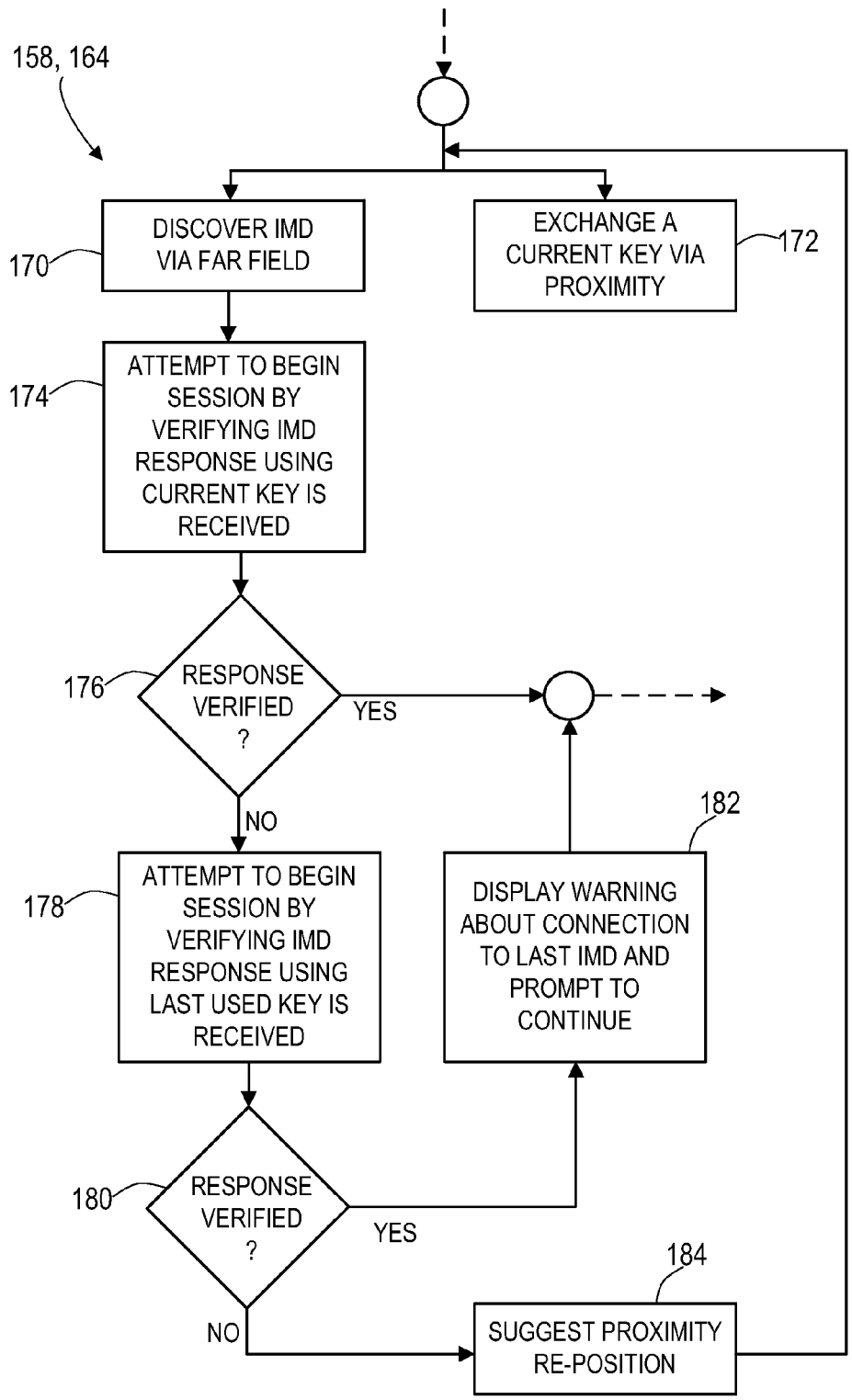
FIG. 6 shows an example of logical operations for embodiments of the external device to establish a far field communication session with the IMD.

The details of establishing the first and second far field communication sessions as in operations 158 and 164 are shown in more detail in FIG. 6. Initially, the external device 102 attempts to discover other devices including the IMD 104 that are within far field communication range at an operation 170 by sending a discovery communication that provokes any device in range to respond. The external device 102 contemporaneously attempts to exchange a current, i.e. new, key with the IMD 104 via a proximity communication at an operation 172. This proximity communication may occur before, during, or immediately after the discovery request.

Upon discovering the IMD 104, the external device 102 attempts to begin a communication session by prompting the IMD 104 to respond where the external device 102 expects the response to use the current key that was transferred at the operation 172. Where the operations of FIG. 6 correspond to the operation 158 of FIG. 5 that pertains to the first far field communication session, the current key is successfully transferred because the IMD 104 is present in close proximity to the wand or hoop 106 outside of the sterile field. Therefore, the IMD 104 is able to respond with the appropriate key being used. In that case, the external device 102 receives the response that is using the current key as expected by the external device 102 such that the response is verified at a query operation 176. Operational flow then proceeds on to the next operation in FIG. 5.

The operations of FIG. 6 also correspond to the operation 164 of FIG. 5 that pertains to the second far field communication session, where the current key is not successfully transferred at operation 172. This is because the IMD 104 is no longer present in close proximity to the wand or hoop 106 outside of the sterile field but is instead within the sterile field. Therefore, the IMD 104 is not able to respond to the attempt by the external device 102 to begin the second communication session with the appropriate key. In that case, the external device 102 does not receive a response that is using the current key as expected by the external device 102 such that the response is not verified at the query operation 176. Operational flow therefore proceeds on to an operation 178.

At the operation 178, the external device 102 again attempts to begin a communication session by prompting the IMD 104 to respond where the external device 102 now expects the response to use the last key that was used in the immediately prior communication session instead of the new key. Where the operations of FIG. 6 correspond to the operation 164 of FIG. 5 that pertains to the second far field communication session, the response by the IMD uses the last used key because the IMD 104 has not received any newer key and therefore continues to use the last used key when responding to the external device 102. In that case, the external device 102 receives the response that is using the last used key as expected by the external device 102 such that the response is verified at a query operation 180.

Upon the external device 102 verifying that the IMD 104 has responded using the last used key instead of the more current key, the external device 102 outputs a warning about the communication session being established with the last IMD at an operation 182. The external device 102 may then prompt the clinician to confirm that the communication session with this last IMD should continue. This operation 182 ensures that the clinician does intend to have the communication session with the last IMD rather than a different IMD. Where the clinician is attempting to program the IMD 104 shortly after the IMD 104 has been implanted such that the IMD 104 is indeed the last IMD that was in a communication session with the external device 102, the clinician will select to continue with the communication session since the last IMD is the correct IMD for the second far field session. However, if the clinician sees this warning at operation 182 for an attempt at a first communication session with a particular IMD, then the clinician will cancel the communication session because the last IMD is not the correct IMD for the session.

Returning to the query operation 180, if the attempt to start the communication session at operation 170 is not verified because no response is received that utilizes the last used key, then operational flow proceeds to an operation 184. The external device 102 then provides a message to the clinician that suggests that the proximity wand or hoop 106 be repositioned because the IMD does not have either the current key or the last used key. The operations may then repeat. Where the IMD 104 is still outside of the sterile field, which is likely to be the case at this point since an IMD 104 inside the sterile field has previously received the key when outside the sterile field, the clinician adjusts that position of the wand or hoop 106 and the current key is then successfully transferred at the next instance of the operation 172. The response is then able to be verified at operation 176.

The operational flow of FIG. 5 is one particular example. In other examples, one or more communication sessions with the ENS may happen at any time where each communication session with the ENS is not treated as a communication session with an IMD such that the attempt to exchange a new key does not occur and the ability to attempt to use the last key is not adversely affected. For instance, the far field session may first occur with the IMD 104, then the session with the ENS occurs, and then a subsequent far field session with the IMD 104 occurs and utilizes the same key as the prior far field session with the IMD 104.

Furthermore, the process shown in FIGS. 5 and 6 is useful in other contexts than during implantation. For instance, the same process may be useful while the patient is in the recovery room and is positioned in such a way that a near field communication cannot be performed. Therefore, the failed attempt to exchange a new key results in the external device 102 beginning a far field session using the last key that was used with the IMD 104 during the implantation procedure.

As an additional safeguard, each key that is exchanged between the external device 102 and the IMD 104 may have a limited lifetime. The IMD 104 may keep track of whether the key that the IMD 104 has received has expired. If the key has expired, then the IMD 104 does not use that key when responding to any attempt by the external device to start a far field communication session. Therefore, any subsequent sessions with that IMD requires a new key to be exchanged via a proximity communication.

While embodiments have been particularly shown and described, it will be understood by those skilled in the art that various other changes in the form and details may be made therein without departing from the spirit and scope of the invention.

What is claimed is:

1. A method of an external device communicating with an implantable medical device where the external device includes a proximity communication circuit, a far field communication circuit, and a controller that is coupled to and controls the proximity communication circuit and the far field communication circuit, the method comprising:
   exchanging a key with the implantable medical device over a first proximity communication;
   beginning a first far field communication session with the implantable medical device and exchanging communications during the first far field communication session with the implantable medical device where the implantable medical device implements the key when exchanging the communications;
   terminating the first far field communication session;
   sending a second key from the external device over a second proximity communication after terminating the first communication session;
   sending a first far field communication from the external device in an attempt to begin a second far field communication session where the external device expects communications of the second far field communication session, including a response to the first far field communication, to use the second key;
   determining if the response to the first far field communication is received and if no response to the first far field communication is received, then sending a second far field communication from the external device in an attempt to begin the second far field communication session where the external device expects communications of the second far field communication session, including a response to the second far field communication, to use the first key; and
   determining if the response to the second far field communication is received and if the response that uses the first key is received in response to the second far field communication, then conducting the second far field communication session where communications of the second far field communication session use the first key.

2. The method of claim 1, wherein during the first far field communication session the implantable medical device is located outside a sterile field during an implantation procedure and during the second far field communication session the implantable medical device is located inside the sterile field during the implantation procedure.

3. The method of claim 1, wherein patient identification information is provided to the implantable medical device during the first far field communication session and therapy programming information is provided to the implantable medical device during the second far field communication session.

4. The method of claim 1, further comprising providing a warning message when a response is received to the attempt to begin the second far field communication session where communications of the second far field communication session, including the response to the attempt, use the first key.

5. The method of claim 1, wherein the first key has an expiration period monitored by the implantable medical device.

6. The method of claim 1, wherein the first and second proximity communications are unidirectional.

7. An external device that communicates with an implantable medical device, comprising:
   a proximity communication circuit;
   a far field communication circuit;
   a controller coupled to the proximity communication circuit and the far field communication circuit, the controller being configured to:
   exchange a key with the implantable medical device over a first proximity communication,
   begin a first far field communication session with the implantable medical device and exchange communications during the first far field communication session with the implantable medical device where the implantable medical device implements the key when exchanging the communications, terminate the first far field communication session, send a second key over a second proximity communication after terminating the first communication session, after sending the second key, send a first far field communication in an attempt to begin a second far field communication session where the controller expects communications of the second session, including a response to the first far field communication, to use the second key, determining if the response to the first far field communication is received and if no response to the first far field communication is received, then send a second far field communication in an attempt to begin the second far field communication session where the controller expects the communications of the second session, including the response to the second far field communication, to use the first key, and determine if the response to the second far field communication is received and if the response that uses the first key is received in response to the second far field communication, then conduct the second far field communication session where communications of the second far field communication session use the first key.

8. The external device of claim 7, wherein the controller is configured to provide patient identification information to the implantable medical device during the first communication session and provide therapy programming information to the implantable medical device during the second far field communication session.

9. The external device of claim 7, wherein the controller is configured to provide a warning message when a response is received to the attempt to begin the second far field communication session where communications of the second far field communication session, including the response to the second far field communication, use the first key.

10. The external device of claim 7, wherein the controller discards the first key upon establishing a far field communication session using the second key.

11. The external device of claim 7, wherein the first and second proximity communications are unidirectional.

12. A system, comprising:

an implantable medical device; and an external device, the external device comprising a proximity communication circuit, a far field communication circuit, and a controller coupled to the proximity communication circuit and the far field communication circuit, the controller being configured to:

exchange a key with the implantable medical device over a first proximity communication, begin a first far field communication session with the implantable medical device and exchange communications during the first far field communication session with the implantable medical device where the implantable medical device implements the key when exchanging the communications, terminate the first far field communication session, send a second key over a second proximity communication after terminating the first communication session, after sending the second key, send a first far field communication in an attempt to begin a second far field communication session where the controller expects communications of the second session, including a response to the first far field communication, to use the second key, determining if the response to the first far field communication is received and if no response to the first far field communication is received, then send a second far field communication in an attempt to begin the second far field communication session where the controller expects the communications of the second session, including the response to the second far field communication, to use the first key, and determine if the response to the second far field communication is received and if the response that uses the first key is received in response to the second far field communication, then conduct the second far field communication session where communications of the second far field communication session use the first key.

13. The system of claim 12, wherein the controller is configured to provide patient identification information to the implantable medical device during the first far field communication session and provide therapy programming information to the implantable medical device during the second far field communication session.

14. The system of claim 12, wherein the controller is configured to provide a warning message when a response is received to the attempt to begin the second far field communication session where communications of the second far field communication session, including the response to the second far field communication, use the first key.

15. The system of claim 12, wherein the first key has an expiration period that is monitored by the implantable medical device.

16. The system of claim 12, wherein the proximity communications are unidirectional.

17. The system of claim 12, wherein the controller discards the first key upon establishing the second far field communication session using the second key.

* * * * *